United States Patent [19]

Oude Alink et al.

[11] 4,163,646

[45] Aug. 7, 1979

[54] FUEL OILS CONTAINING N,N-SUBSTITUTED DIAMINES

[75] Inventors: Bernardus A. Oude Alink, St. Louis; Neil E. S. Thompson, Crève Coeur, both of Mo.

[73] Assignee: Petrolite Corporation, St. Louis, Mo.

[21] Appl. No.: 755,535

[22] Filed: Dec. 30, 1976

Related U.S. Application Data

[62] Division of Ser. No. 597,564, Jul. 21, 1975, and Ser. No. 292,494, Sep. 27, 1972, Pat. No. 4,085,104.

[51] Int. Cl.$^2$ .................................................. C10L 1/22
[52] U.S. Cl. ............................................................ 44/73
[58] Field of Search ............... 44/74, 72; 260/583 R, 260/563 R, 570.5 P

[56] References Cited

U.S. PATENT DOCUMENTS

| | | | |
|---|---|---|---|
| 2,264,894 | 12/1941 | Shoemaker et al. | 44/73 |
| 2,301,861 | 11/1942 | Downing et al. | 44/73 |
| 2,305,675 | 12/1942 | Chenicek | 44/74 |
| 2,333,294 | 11/1943 | Chenicek | 44/72 |
| 3,207,789 | 9/1965 | Mathews | 44/72 |
| 3,490,882 | 1/1970 | Dunworth | 44/72 |
| 3,523,769 | 8/1970 | Tooke | 44/72 |

*Primary Examiner*—Patrick Garvin
*Assistant Examiner*—Mrs. Y. Harris-Smith
*Attorney, Agent, or Firm*—Sidney B. Ring; Hyman F. Glass

[57] ABSTRACT

This invention relates to the hydrogenation of tetrahydropyrimidines to yield linear N-substituted diamines which can be reacted with carbonyls to form imines, which imines can be reduced to N,N'-substituted diamines as illustrated by N,N'-substituted 2,4-diamino-2-substituted pentanes. The products of this invention are useful as fuel additives.

14 Claims, No Drawings

FUEL OILS CONTAINING N,N-SUBSTITUTED DIAMINES

This application is a division of Ser. No. 597,564 filed July 21, 1975 and a division of Ser. No. 292,494 filed Sept. 27, 1972, now U.S. Pat. No. 4,085,104.

In Ser. No. 292,494 filed on Sept. 27, 1972, now U.S. Pat. No. 4,085,104, there is described and claimed substituted 2, 3, 4, 5-tetrahydropyrimidines (THP)

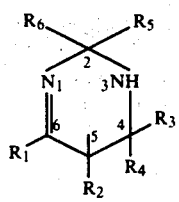

Formula I which are prepared by the following reactions:

(1) The reaction of a carbonyl compound (ketone or aldehyde) with ($NH_3$ or $NH_4OH$) and a sulfur-containing catalyst.

(2) The reaction of an $\alpha,\beta$-unsaturated ketone and a carbonyl compound and $NH_3$ (or $NH_4OH$) without a catalyst.

(3) Reaction of an $\alpha,\beta$-unsaturated ketone, a 1-aminoalcohol and $NH_3$ (or $NH_4OH$) without a catalyst.

In the above formula, $R_1$, $R_2$, $R_3$, $R_4$, $R_5$ and $R_6$, which may be the same or different, are hydrogen or substituted group such as alkyl, aryl, cycloalkyl, alkaryl, aralkyl, heterocyclic, substituted derivatives thereof, etc. In addition R groups may be joined in a cyclic configuration which makes the THP structure a part of the substituted group.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, etc., for example having about 1–25 or more carbons such as from about 1–18 carbons, but preferably about 1–12 carbons. The term "alkyl" also includes isomers of the straight chain where branching occurs.

Cycloalkyl includes cyclopentyl, cyclohexyl, etc., and derivatives thereof such as alkyl-cyclohexyl, dialkylcyclohexyl, etc.

Aryl, alkaryl and aralkyl, including phenyl, alkylphenyl, polyalkylphenyl, chlorophenyl, alkoxyphenyl, naphthyl, alkylnaphthyl, etc., benzyl, substituted benzyl, etc.

The joining of the R groups into a ring structure include those structures derived from reactants of the general formula

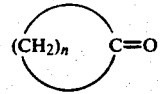

such as cyclohexanone, cyclopentanone, substituted derivatives thereof such as alkyl-cyclohexanone, dialkyl-cyclohexanone.

We have now discovered that the 2,2-di-substituted derivatives of Formula I can be converted to linear diamines such as N-substituted-2,4-diamino-2-substituted pentanes by hydrogenation.

We have further discovered that such reaction occurs only with the 2,2-di-substituted tetrahydropyrimidines. Where the 2,2-di-substitution is not present, the corresponding cyclic hexahydropyrimidines are formed instead of the linear diamines.

We have further discovered that a compound of Formula II can be converted to an amine-imine by reacting with a carbonyl compound.

We have also discovered the amine-imine can be converted to the corresponding N,N'-substituted diamines by hydrogenation.

These reactions may be summarized as follows:

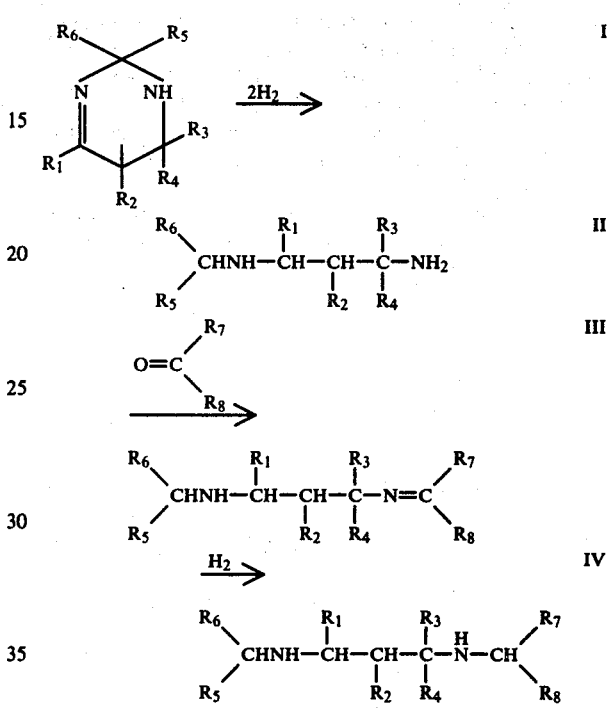

or more specifically as follows:

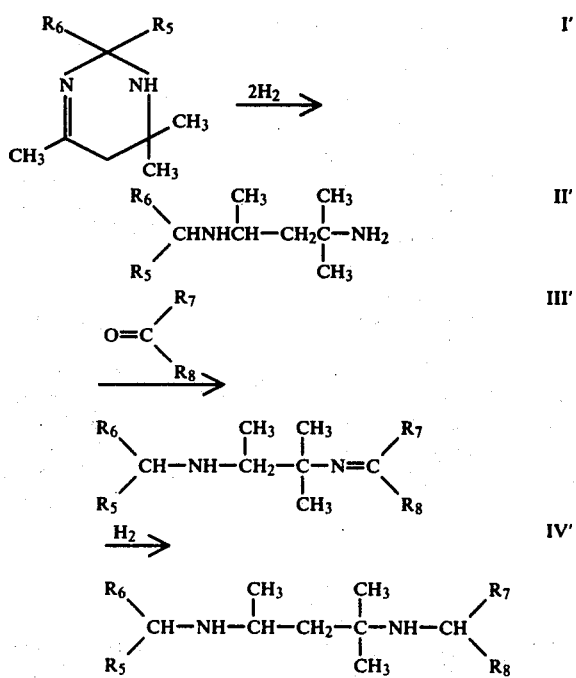

Although the above reactions are illustrated with the trimethyl tetrahydropyrimidine, the methyl groups may be replaced with other groups such as for example hydrogen, higher alkyls, aryls, cycloalkyls, etc.

The hydrogenation reaction is carried out in the presence of a hydrogenation catalyst such as palladium, platinum, nickel, etc.; at a suitable temperature, for example from ambient to 200° C. or higher, but preferably 50°–150° C.; at pressures sufficient to contain hydrogen in the reaction vessel, such as about 10–2000 psi, or higher but preferably about 200–1000 psi; for a sufficient period of time for the reaction to take place such as from about 10 minutes to 24 hrs. or longer, preferably from about ½ hr. to 6 hrs.; in solvents which do not interfere with the catalyst, reactants, or products such as water, alcohol, hydrocarbons, esters, etc.

In addition, reduction can be effected with compositions which on reaction yield hydrogen such as metal hydrides, etc.

The linear amine resulting from hydrogenation is then reacted with a carbonyl compound of the formula

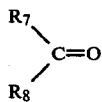

which is either an aldehyde or a ketone.

The preparation of the imine compound is conventional. For example the reaction can be carried out by heating the amine with substantially stoichiometric amounts of the carbonyl compound under dehydrating conditions, i.e., 1:1 molar ratio, for example by the use of an azeotroping agent.

The imine compound resulting from the carbonyl reaction can be further reduced in the manner of Step 1 to yield the substituted diamine.

In the above formula, $R_7$ and $R_8$, which may be the same or different, are hydrogen or substituted group such as alkyl, aryl, cycloalkyl, alkaryl, aralkyl, heterocyclic, substituted derivatives thereof, etc. In addition R groups may be joined in a cyclic configuration.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, etc., for example having about 1–25 or more carbons such as from about 1–18 carbons, but preferably about 1–12 carbons. The term "alkyl" also includes isomers of the straight chain where branching occurs.

Cycloalkyl includes cyclopentyl, cyclohexyl, etc., and derivatives thereof such as alkyl-cyclohexyl, dialkylcyclohexyl, etc.

Aryl, alkaryl and aralkyl include phenyl, alkylphenyl, polyalkylphenyl, chlorophenyl, alkoxyphenyl, naphthyl, alkylnaphthyl, etc., benzyl, substituted benzyl, etc.

The joining of the R groups into a ring structure include those structures derived from reactants of the general formula

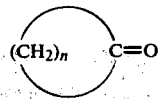

such as cyclohexanone, cyclopentanone, substituted derivatives thereof such as alkyl-cyclohexanone, dialkyl-cyclohexanone.

The following examples are presented for purposes of illustration and not of limitation.

EXAMPLE 1

N-Cyclohexyl-2,4-diamino-2-methylpentane

In a 1 liter stirred autoclave was placed 95 g of 2,2-pentamethylene-4,4,6-trimethyl-2,3,4,5-tetrahydropyrimidine, 200 cc. of methanol and 6 g of 5% Pt/C catalyst. The autoclave was pressurized with 400 psi of hydrogen gas and the mixture heated for 75 minutes at 75°–80° C. while a pressure of 400–800 psi was maintained. The reaction product was removed through an internal filter leaving the catalyst behind. After removal of the solvent, there was isolated 95 g of N-cyclohexyl 2,4-diamino-2-methylpentane.

The analytical data were consistent with the assigned structure

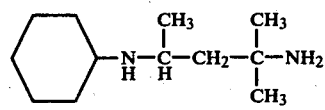

Anal. calcd for $C_{12}H_{26}N_2$; N, 14.14. Found: N, 13.98.

EXAMPLE 2

N-Cyclohexyl, N'-isobutyl 2,4-diamino-2-methylpentane

A sample of 50 g of N-cyclohexyl -2,4-diamino-2-methylpentane and 18.7 g of isobutyraldehyde in 50 cc of benzene was refluxed under azeotropical conditions for 1 hr. The benzene was removed under diminished pressure to yield 67 g of product. The product was dissolved in 200 cc of methanol and 9.6 g of sodium boronhydride was slowly added with stirring. After the reaction was completed, the solvent was removed under diminished pressure. To the resulting product was added water and the organic layer was separated. The aqueous layer was extracted with ether and the ethereal solution combined with the organic layer. After removal of the ether under diminished pressure the product was distilled under diminished pressure to yield 60 g of N-Cyclohexyl, N'-isobutyl 2,4-diamino-2-methylpentane, $b_{0.6}=98°$ C.

Anal. calcd. for $C_{16}H_{32}N_2$; N, 11.11. Found: N, 11.01. The analytical data were consistent with the assigned structure

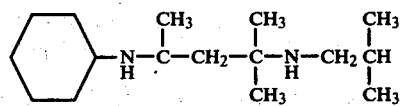

EXAMPLE 3

N-Cyclohexyl, N' isobutyl 2,4-diamino-2-methylpentane and 18.7 g of isobutyraldehyde in 50 cc of benzene was refluxed under azeotropical conditions for 1 hour. After removal of the solvent, the product was dissolved in 100 cc of methanol and placed with 2 g of a 10% Pt/C catalyst in an autoclave. The reaction was pressurized with 400 psi of hydrogen and the mixtue was heated with stirring for 3 hrs. at 75°–80° C. After removal of the catalyst by filtration, the methanol was removed under diminished pressure to yield 67 g of N-Cyclohexyl, N'-isobutyl 2,4-diamino-2-methylpentane, identical in all respects to the product isolated as described in example 2.

EXAMPLE 4

N-Cyclohexyl, N'-isobutyl 2,4-diamino-2-methylpentane

In a 1 liter stirred autoclave was placed 95 g of 2,2-pentamethylene 4,4,6-trimethyl 2,3,4,5-tetrahydropyrimidine, 200 cc of methanol and 6 g of 5% Pt/C catalyst. The mixture was hydrogenated with stirring for 60 minutes at 75°–80° C. and 400–800 psi of hydrogen. To the mixture was added 39 g of isobutyraldehyde and hydrogenation was continued for 3 hrs. at 75°–80° C. and 400–800 psi of hydrogen pressure. The catalyst was removed and the mixture evaporated under diminished pressure, to yield 116 g of N-cyclohexyl, N'-isobutyl 2,4-diamino-2-methylpentane, identical in all respects to the product isolated as described in example 2.

The following 2,4-diamino-2-methylpentanes were prepared, according to the methods described in examples 1–4. The results are summarized in Table I.

Table I:

General Structure:

$$R_1-\underset{H}{\underset{|}{C}}-\underset{H}{\underset{|}{N}}-\underset{H}{\underset{|}{C}}\underset{CH_3}{\overset{CH_3}{|}} \quad -\underset{H}{\underset{|}{C}}-\underset{|}{\overset{H}{C}}\underset{CH_3}{\overset{CH_3}{|}} \quad -\underset{H}{\underset{|}{N}}-\underset{H}{\underset{|}{C}}-R_4\overset{R_3}{\overset{|}{}}$$

| Ex. No. | $R_1$ | $R_2$ | $R_3$ | $R_4$ |
|---|---|---|---|---|
| 5 | $CH_3$ | $CH_3$ | — | —* |
| 6 | $CH_3$ | $CH_3$ | H | $CH(CH_3)_2$ |
| 7 | $CH_3$ | $CH_3$ | H | $CH_2-CH_2-CH_3$ |
| 8 | $CH_3$ | $CH_3$ | H | Phenyl |
| 9 | $CH_3$ | $CH_3$ | $-CH_2-CH_2-C-(CH_3)-CH_2-CH_2-$ | |
| 10 | $CH_3$ | $C_2H_5$ | — | —* |
| 11 | $CH_3$ | $C_2H_5$ | H | $CH(CH_3)_2$ |
| 12 | $-(CH_2)_5-$ | | H | $C_2H_5$ |
| 13 | $-(CH_2)_5-$ | | H | $CH_2-CH_2-CH_3$ |
| 14 | $-(CH_2)_5$ | | $-(CH_2)_5-$ | |
| 15 | $-(CH_2)_5-$ | | H | Phenyl |
| 16 | $-(CH_2)_5$ | | H | $CH(C_2H_5)_2$ |
| 17 | $-(CH_2)_5-$ | | H | $CH_3$ |
| 18 | $-(CH_2)_5-$ | | $-CH_2-CH(CH_3)-CH_2-CH_2-CH_2-$ | |
| 19 | $-(CH_2)_5-$ | | $-CH_2-CH_2-CH(CH_3)-CH_2-CH_2-$ | |

*where $R_3$
$\underset{H}{\underset{|}{C}}-R_4=H$

USE AS FUEL ADDITIVE

As is well known, fuel oils have a tendency to deteriorate in storage and form soluble colored bodies and insoluble sludge therein. This deterioration of the oil is highly undesirable in that it causes serious adverse effects on the characteristics of the oil, particularly on the ignition and burning qualities thereof. It is also a contributory factor, along with the presence of other impurities in the oil, such as rust, dirt and moisture, in causing clogging of the equipment parts, such as screens, filters, nozzles, etc., as is explained further herein. An important economical factor is also involved in the problem of oil deterioration in storage, viz., customer resistance. Thus, customers judge the quality of an oil by its color and they oftentimes refuse to purchase highly colored oils. It will be appreciated then that since fuel oils of necessity are generally subject to considerable periods of storage prior to use, the provision of a practical means for preventing the deterioration of the fuel oil during storage would be a highly desirable and important contribution to the art.

The problem of the formation of color bodies and sludge is further aggravated because fuels, such as diesel and jet fuels, are often preheated for some time before consumption, thus introducing the additional problem of thermal instability.

It has now been found that oil deterioration, with attendant formation of color and sludge in the oil, can be inhibited by employing the additives of this invention in the oil. In general, one employs a minor amount of the additive which is sufficient to inhibit oil deterioration with the attendant formation of color and sludge.

The amount of additive employed will vary depending on various factors, for example the particular oil to be stabilized, the conditions of storage, etc. The stability of an oil depends largely on the nature of the crude oil from which it is made, the type of processing involved during refining, etc., and therefore some oils will require more additive to stabilize them than others. For example, caustic-treated oil will, in general, require less additive than untreated oil of similar character. In practice, one generally employs at least about 0.0001% (1 p.p.m.), such as from about 0.0001 to 0.1% (1–1000 p.p.m.), for example about 0.0002 to 0.05% (2–500 p.p.m.), but preferably about 0.0003 to 0.03% (3–300 p.p.m.) based on weight of oil. Larger amounts, such as 1% or higher, can be employed but in general there is usually no commercial advantage in doing so.

Fuel oils in general are contemplated by the invention. The fuel oils with which this invention is especially concerned are hydrocarbon fractions having an initial boiling point of at least about 100° F. and an end point not higher than about 750° F., and boiling substantially continuously throughout their distillation range. Such fuel oils are generally known as distillate fuel oils. It will be understood, however, that this term is not restricted to straight-run distillate fractions. Thus, as is well known to those skilled in the art, the distillate fuel oils can be straight-run distillate fuel oils, catalytically or thermally cracked (including hydrocracked) distillate fuel oils, or mixtures of straight-run distillates, naphthas and the like, with cracked distillate stocks. Moreover, such fuel oils can be treated in accordance with well known commercial methods, such as acid or caustic treatment, solvent refining, clay treatment, etc.

The distillate fuel oils are characterized by their relatively low viscosities, low pour points, and the like. The principal property which characterizes the contemplated hydrocarbon fractions, however, is the distillation range. As mentioned herein, this range will lie between about 100° F. and about 750° F. Obviously, the distillation range of each individual fuel oil will cover a narrower range falling, nevertheless, within the above-specified limits. Likewise, each fuel oil will boil substantially continuously throughout its distillation range.

Especially contemplated herein are Nos. 1, 2 and 3 fuel oils used in domestic heating and as diesel fuel oils, particularly those made up chiefly or entirely of cracked distillate stocks. The domestic heating oils generally conform to the specifications set forth in A.S.T.M. Specifications D396-48T. Specifications for diesel fuels are defined in A.S.T.M. Specifications D975-48T. Also contemplated herein are fuels for jet combustion engines. Typical jet fuels are defined in Military Specification MIL-F-5624B.

The following diesel fuel test is a standard test for diesel fuel stability and is regarded as a rapid screening test for discovering new systems, which can be used to stabilize petroleum distillate fuels.

DIESEL FUEL TEST

90 minutes @ 300° F.

In the operation of a diesel engine, a portion of the fuel sent to the fuel injection system is injected and burned; the remainder is circulated back to the fuel reservoir. The injection system is located on the engine such that the fuel being returned to the reservoir is subjected to high temperatures. Consequently, diesel fuels should exhibit good thermal stability as well as good storage stability. Since the fuels used as diesel fuel are interchangeable with furnace oils, the following procedure is used to screen the thermal stability of fuel oils in general.

The test involves exposing 50 ml. samples of fuel, containing desired quantities of fuel additives, to the test where a bath is held at 300° F. and the samples are exposed for 90 minutes.

After cooling to room temperature the exposed fuel is passed through a moderately retentive filter paper and the degree of stain on the filter paper noted. The filter paper pads are compared according to a rating of 1=best and 20 worst.

The results are presented in the following Table.

| Product of example no. | Fuel A 20ppm additive | Fuel B 20ppm additive | Fuel C 5ppm additive |
|---|---|---|---|
| no additive | 18 | 18 | 11 |
| 14 | 4 | 4 | 4 |
| 4 | 3 | 4 | 2 |
| 2 | 4 | 5 | 2 |
| 3 | 3 | 4 | 2 |
| 13 | 4 | 5 | 3 |
| 12 | 4 | 5 | 4 |
| 16 | 5 | 5 | 3 |
| 17 | 4 | 5 | 3 |
| 18 | 5 | 4 | 5 |
| 19 | 7 | 4 | 4 |
| 9 | 8 | 5 | 9 |

Ratings: from 1-20 where
1 = white filter - no residue stains, and
20 = black filter - heavy residue stains Although the additives of this invention are useful as fuel additives per se their performance may be enhanced by employing certain auxiliary chemical aids. Among these chemical aids are dispersants, for example acrylic polymers or copolymers which can be employed in conjunction with the cyclohexylamines.

One such auxiliary chemical component is the copolymer derived from an acrylic ester of the formula:

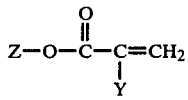

and N-vinyl-2-pyrrolidone, for example a copolymer containing the following units:

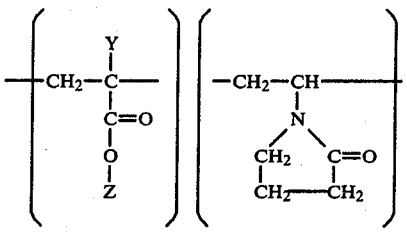

having a molecular weight for example of at least 50,000, for example 50,000–500,000, or higher, but preferably 100,000–400,000 with an optimum of 300,000–400,000 of which vinyl pyrrolidone comprises at least 1% by weight, of the polymer, for example 1–30%, but preferably 3–15% with an optimum of 5–10%; where Y is hydrogen, a lower alkyl group such as methyl, ethyl, etc., Z is an hydrocarbon group having, for example, 1–30 carbon atoms, but preferably 8 to 18 carbon atoms. These polymers are preferably acrylic or methacrylic polymers, or polymers derived from both in conjunction with vinyl pyrrolidone. The Z group on the polymer, which can be the same throughout or mixed, can be octyl, nonyl, decyl, undecyl, dodecyl, tridecyl, tetradecyl, pentadecyl, octadecyl, etc. Lower alkyl groups can also be employed such as methyl, ethyl, propyl, butyl, pentyl, hexyl, heptyl, etc., but they preferably are employed as copolymers of the higher Z groups, for example a copolymer of dodecyl methacrylate and methyl acrylate, etc. The acrylic ester units may be derived from one or more acrylic type monomers and may be fully acrylic or fully methacrylic or both acrylic and methacrylic. The polymer may be random, block, graft, etc.

Z may also be an alkylated aromatic group such as butyl phenyl, amyl phenyl, etc., or a cycloaliphatic group such as cyclohexyl. Thus, non-limiting specific examples of suitable monomeric esters are: methyl acrylate, ethyl acrylate, propyl methacrylate, amyl acrylate, lauryl acrylate, cetyl acrylate, octadecyl acrylate, amyl methacrylate, lauryl methacrylate, cetyl methacrylate, octadecyl methacrylate, amylphenyl methacrylate, cyclohexyl methacrylate, etc., including the analogous acrylate or methacrylate esters. Copolymers of the above and other acrylic esters may be used, for example, a copolymer of methyl or ethyl acrylate and dodecyl methacrylate in conjunction with vinyl pyrrolidone. However, it should be understood that this description does not preclude the presence of small amounts of unesterified groups being present in the polymer, i.e., approximately 5% or less of where Z=H.

It should be understood, of course, that when the above compounds are polymerized, the polymerization should not be carried to such an extent as to form polymers which are insoluble or non-dispersible in the petroleum hydrocarbon used. The polymerization may be carried out by methods known to the art, such as by heating mildly in the presence of a small amount of benzoyl peroxide, but the method of polymerization is not part of this invention. For examples of acrylic-vinyl pyrrolidone copolymers see French Pat. No. 1,163,033.

Example of vinyl pyrrolidone-acrylic ester type resins are presented in the following table:

VINYL PYRROLIDONE-ACRYLIC ESTER TYPE RESINS

| Ex. | Monomer 1 | Monomer 2 | Monomer 3 | Vinyl pyrrolidone, percent by wt. | Mol ratio 1:2:3 | Av. mol weight |
|---|---|---|---|---|---|---|
| 1 | Tridecyl methacrylate | Octadecyl methacrylate | | 7.5 | 1:1 | 300,000 |
| 2 | Dodecyl methacrylate | | | 10 | | |
| 3 | Dodecyl methacrylate | Butyl acrylate | | 15 | 2:1 | 400,000 |
| 4 | Octadecyl methacrylate | | | 5 | | 450,000 |
| 5 | Tridecyl methacrylate | | | 20 | | 350,000 |
| 6 | Octadecyl methacrylate | Methyl methacrylate | | 10 | 3:1 | 500,000 |
| 7 | Dodecyl methacrylate | Ethyl acrylate | | 5 | 4:1 | 400,000 |
| 8 | Cetyl methacrylate | Octadecyl methacrylate | Butyl methacrylate | 7.5 | 2.1:0.5 | 350,000 |

Another auxiliary chemical component is a metal deactivator for example those conveniently employed in deactivating copper, iron and other metals from hydrocarbon systems. Typical examples are those described in U.S. Pat. No. 2,282,513. Of course, one skilled in the art is aware that many other metal deactivators are known and can be employed.

The compounds employed as metal deactivators are preferably of the type of Schiff bases and may be represented by the formulae

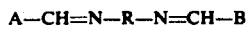   (1)

and preferably,

   (2)

wherein A and B each represents an organic radical and preferably a hydrocarbon radical. In Formula 2 A and B each preferably represents an aromatic ring or an unsaturated heterocyclic ring in which the hydroxyl radical is attached directly to a ring carbon atom ortho to the —CH=N-group. R represents an aliphatic radical having the two N atoms attached directly to different carbon atoms of the same open chain.

Typical examples of aldehyde and polyamines employed in preparing these Schiff bases include the following:

ALDEHYDES

Benzaldehyde
2-methylbenzaldehyde
3-methylbenzaldehyde
4-methylbenzaldehyde
2-methoxybenzaldehyde
4-methoxybenzaldehyde
2-naphthaldehyde
1-naphthaldehyde
4-phenylbenzaldehyde
Propionaldehyde
n-Butyraldehyde
Heptaldehyde
Aldol
2-hydroxybenzaldehyde
2-hydroxy-6-methylbenzaldehyde
2-hydroxy-3-methoxybenzaldehyde
2-4-dihydroxybenzaldehyde
2-6-dihydroxybenzaldehyde
2-hydroxynaphthaldehyde-1
1-hydroxynaphthaldehyde-2
Anthrol-2-aldehyde-1
2-hydroxyfluorene-aldehyde-1
4-hydroxydiphenyl-aldehyde-3
3-hydroxyphenanthrene-aldehyde-4
1-3-dihydroxy-2-4-dialdehyde-benzene
2-hydroxy-5-chlorobenzaldehyde
2-hydroxy-3-5-dibromobenzaldehyde
2-hydroxy-3-nitrobenzaldehyde
2-hydroxy-3-cyanobenzaldehyde
2-hydroxy-3-carboxybenzaldehyde
4-hydroxypyridine-aldehyde-3
4-hydroxyquinoline-aldehyde-3
7-hydroxyquinoline-aldehyde-8

POLYAMINES

Ethylenediamine
1-2-propylenediamine
1-3-propylenediamine
1-6-hexamethylenediamine
1-10-decamethylenediamine
Diethylenetriamine
Triethylenetetramine
Pentaerythrityltetramine
1-2-diaminocyclohexane
Di-(b-aminoethyl)ether
Di-(b-aminoethyl)sulfide The ratio of the additives of this invention to the metal deactivator can vary widely depending on the particular system, the fuel, etc., employed. Thus, the weight ratio of additive to metal deactivator may be from about 0.1 to 20 or more, such as from about 8-15, but preferably from about 10-12.

The weight ratio of additive to the acrylic type polymer can also vary widely from about 0.1-20 or more, such as from 8-15, but preferably from about 10-12.

For ease of handling a concentrate of the additive of this invention in a solvent such as a hydrocarbon, for example in concentrations of 5–75% or higher, such as from 20–60, but preferably from 40–60%.

The additives of this invention may also be used in petroleum products to inhibit the formation of deposits on metal surfaces such as occurs in tubes, evaporators, heat exchangers, distillation and cracking equipment and the like.

We claim:

1. Fuel oil containing a stabilizing amount of a stabilizer consisting of a compound of the formula

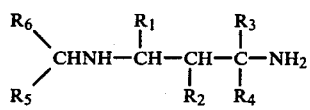

where $R_5$ and $R_6$ are groups selected from the group consisting of alkyl, aryl, cycloalkyl, alkaryl, and aralkyl and $R_1$, $R_2$, $R_3$, and $R_4$ are hydrogens or a group selected from the group consisting of alkyl, aryl, cycloalkyl, alkaryl and aralkyl.

2. Fuel oil containing a stabilizing amount of a stabilizer consisting of a compound of the formula

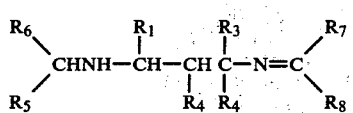

where $R_5$, $R_6$ and $R_7$ are groups selected from the group consisting of alkyl, aryl, cycloalkyl, alkaryl and aralkyl and $R_1$, $R_2$, $R_3$, $R_4$ and $R_8$ are hydrogens or a group selected from the group consisting of alkyl, aryl, cycloalkyl, alkaryl and aralkyl.

3. Fuel oil containing a stabilizing amount of a stabilizer consisting of a compound of the formula

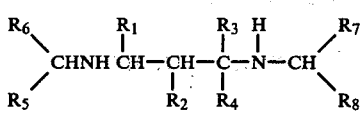

where $R_5$, $R_6$ and $R_7$ are groups selected from the group consisting of alkyl, aryl, cycloalkyl, alkaryl and aralkyl and $R_1$, $R_2$, $R_3$, $R_4$ and $R_8$ are hydrogen or a group selected from the group consisting of alkyl, aryl, cycloalkyl, alkaryl and aralkyl.

4. Fuel oil of claim 1 where $R_1$, $R_3$ and $R_4$ in the compound are alkyl.

5. Fuel oil of claim 2 where $R_1$, $R_3$ and $R_4$ in the compound are alkyl.

6. Fuel oil of claim 3 where $R_1$, $R_3$ and $R_4$ in the compound are alkyl.

7. Fuel oil of claim 4 where $R_1$, $R_3$ and $R_4$ in the compound are methyl.

8. Fuel oil of claim 5 where $R_1$, $R_3$ and $R_4$ in the compound are methyl.

9. Fuel oil of claim 6 where $R_1$, $R_3$ and $R_4$ in the compound are methyl.

10. Fuel oil of claim 7 where $R_5$ and $R_6$ in the compound are aryl, alkyl, or are joined to form a cycloalkyl group.

11. Fuel oil of claim 8 where $R_5$ and $R_6$ in the compound are aryl, alkyl, or are joined to form a cycloalkyl group and $R_7$ is alkyl, aryl, or joined with $R_8$ to form a cycloalkyl group and $R_8$ is hydrogen or alkyl, aryl, or joined with $R_7$ to form a cycloalkyl group.

12. Fuel oil of claim 9 where $R_5$ and $R_6$ in the compound are aryl, alkyl, or are joined to form a cycloalkyl group and $R_7$ is alkyl, aryl, or joined with $R_8$ to form a cycloalkyl group and $R_8$ is hydrogen or alkyl, aryl, or joined with $R_7$ to form a cycloalkyl group.

13. Fuel oil of claim 10 containing a stabilizing amount of a stabilizer consisting of at least one compound of the formula

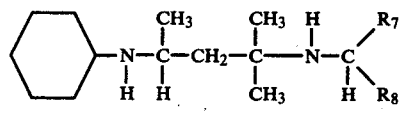

where $R_7$ and $R_8$ are joined to form a cyclic hexyl or methyl substituted cyclohexyl group.

14. Fuel oil of claim 12 containing a stabilizing amount of a stabilizer consisting of a compound of the formula

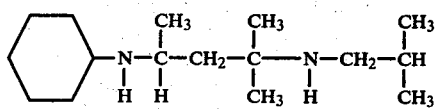

* * * * *